US006213127B1

(12) United States Patent
Waller

(10) Patent No.: US 6,213,127 B1
(45) Date of Patent: Apr. 10, 2001

(54) METHODS FOR TREATING CANCER USING ALLOGENEIC LYMPHOCYTES WITHOUT GRAFT VS HOST DISEASE ACTIVITY

(75) Inventor: Edmund K. Waller, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/068,472

(22) PCT Filed: Jul. 29, 1996

(86) PCT No.: PCT/US96/12426

§ 371 Date: Sep. 3, 1998

§ 102(e) Date: Sep. 3, 1998

(87) PCT Pub. No.: WO97/17079

PCT Pub. Date: May 15, 1997

(51) Int. Cl.$^7$ .................................................... A61B 19/00
(52) U.S. Cl. ............................................ 128/898; 424/527
(58) Field of Search .............................. 424/527; 623/11; 128/898; 604/500

(56) References Cited

U.S. PATENT DOCUMENTS

| 4,869,826 | 9/1989 | Wang et al. . |
| 5,032,508 | 7/1991 | Naughton et al. . |
| 5,147,289 | 9/1992 | Edelson . |
| 5,601,815 | 2/1997 | Powire et al. . |

FOREIGN PATENT DOCUMENTS

| WO 92/10198 | 6/1992 | (WO) . |
| WO9210198 | 6/1992 | (WO) . |
| WO 94/26284 | 11/1994 | (WO) . |
| WO9426284 | 11/1994 | (WO) . |
| WO 95/12404 | 5/1995 | (WO) . |
| WO 95/24910 | 9/1995 | (WO) . |

OTHER PUBLICATIONS

Gratwohl et al. "Engraftment of T–Cell–Depleted Rabbit Bone Marrow" 1987, ACTA Haematologica, vol. 77, No. 4, pp. 208–14.

Gratwohl et al. "Irradiated Donor Buffy Coat Following T Cell–Depleted Bone Marrow Transplants" 1988, Bone Marrow Transplantation, vol. 3, pp. 577–82.

Cohn et al "Hematopoietic Reconstitution and Prevention of Graft–Versus–Host Disease with UVB–Irradiated Haploidentical Murine Spleen and Marrow Cells" 1991, Blood, vol. 78, pp. 3317–22.

Kochupillai "Emeging Concepts in the Management of Acute Lymphoblastic Leukaemia" 1993, Indian Journal of Medical Research (B), vol. 98, pp. 1–7.

Kochupillani, V. "Emerging Concepts in the Management of Acute Lymphoblastic Leukaemia" Indian J Med Res 98, pp. 1–7, Feb.1993.

Cohn et al. "Hamatopoietic Reconstruction and Prevention of Graft–Versus–Host Disease with UVB–Irradiated Haploidentical Murine Spleen and Marrow Cells" Blood 78(12):3317–3322, Dec. 15, 1991.

Storb et al. ( Jul. 1968) "Marrow grafts by combined marrow and leukocyte infusions in unrelated dogs selected by histocompatability typing" Transplatation 6(4):587–593.

Deeg et al. (Apr. 1979) "Abrogation of resistance to and enhancement of DLA–nonidentical unrelated marrow grafts in lethally irridated dogs by thoracic duct lymphocytes" Blood 53(4):552–557.

Gratwohl et al. (1987) "Engraftment of T–cell depleted rabbit bone marrow" Acta bactomal, 77:208–214.

Storb et al. (Feb. 1982) "Marrow transplatation with or without donor buffy caot cells for 65 transfused aplastic anemia patients" Blood 59(2):236–246.

Gratwohl et al. (1988) "Irradiated donor buffy coat following T cell–depleted bone marrow transplants" Bone Marrow Transplation 3:577–582.

Till and mcCulloch (1961) "A direct measurement of the radiation sensitivity of normal mouse bone marrow cells" Radiation Res. 14:213–222.

Blazar et al. (1985) "Comparison of three techniques for the ex vivo elimination of T cells from human bone marrow," Experimental Hematology 13:123–128.

Baum et al. (Apr. 1992) "Isolation of a candidate human hematipoietic stem–cell population" Proc. Natl. Acad. Sci. U.S.A. 89:2804–2808.

Lansdorp et al. (Jul. 1990) "Selective expression of CD45 isoforms on functional subpopulations of CD34 hemopoietic cells from human bone marrow" J. Exp. Med. 172:363–366.

Sato et al. (Aug. 1991) "Purification of human bone marrow progenitor cells and dmonstration of the direct action of macrophage colony–stimulating factor on colony–forming unit–macrophage" Blood 78(4):967–974.

(List continued on next page.)

Primary Examiner—V. Millin
Assistant Examiner—Kelley O'Hara
(74) Attorney, Agent, or Firm—Needle & Rosenberg, P.C.

(57) ABSTRACT

The present invention provides a method of transplanting hematopoietic system reconstituting cells from a donor into an allogeneic recipient comprising administering to the recipient, prior to the administration of the hematopoietic system reconstituting cells, an amount of mononuclear cells which are treated so as to render them incapable of proliferating and causing a lethal graft versus host disease effect, but which are effective in enhancing subsequent engraftment of the hematopoietic system reconstituting cells in the recipient; and administering to the recipient an effective amount of hematopoietic system reconstituting cells.

44 Claims, No Drawings

OTHER PUBLICATIONS

Smith et al. (May 1991) "Purification and partial charaterization of a human hematopoietic precursor population" Blood 77(10):2122–2128.

Udomsakdi ey al. (1991) "Separation of functionally distinct subpopulations of primitive human hematopoietic cells using rhodamine–123" Exp. Hematol. 19:338–342.

Udomsakdi et al. (Nov. 1992) "Characterization of primitive hematopoietic cells in normal human peripheral blood" Blood 80(10):2513–2521.

Waller et al. (Nov. 1991) "Growth of primary T–cell non––Hodgkin's lymphomata in SCID–hu mice: requirement for a human lymphoid microenvironment" Blood 78(10):2650–2665.

Storb et al. (Aug. 1994) "CyClophosphamide combined with antuthymocyet globulin in preparation for allogenic marrow transplants in patients with aplastic anemia" Blood 84(3):941–949.

METHODS FOR TREATING CANCER USING ALLOGENEIC LYMPHOCYTES WITHOUT GRAFT VS HOST DISEASE ACTIVITY

The present application is a 35 U.S.C. § 371 national phase continuation-in-part application filed from international patent application PCT/US96/12426, filed Jul. 29, 1996, which claims priority to patent application U.S. Ser. No. 08/555,520, filed Nov. 8, 1995, now U.S. Pat. No. 5,800,539, issued Sep. 1, 1998.

BACKGROUND OF THE INVENTION

1. Field of the Invention

The present invention relates to a method of transplanting hematopoietic system reconstituting cells between genetically unrelated individuals using a combination of treated mononuclear cells and bone marrow or peripheral blood hematopoietic system reconstituting cells.

2. Background Art

Allogeneic bone marrow transplantation is the preferred treatment for a variety of malignant and genetic diseases of the blood and blood-forming cells. The widespread application of this therapy is limited by the availability of suitable bone marrow donors who are genetically related to the patient and share the same transplantation antigens on the surface of their blood cells. Only 25% of patients have a sibling who is an antigenically matched potential donor. Bone marrow transplantation can be offered to those patients who lack an appropriate sibling donor by using bone marrow from antigenically matched, genetically unrelated donors (identified through a national registry), or by using bone marrow from a genetically related sibling or parent whose transplantation antigens differ by one to three of six human leukocyte antigens from those of the patient. However, using antigenically mismatched, genetically related parent or sibling or antigenically matched, genetically unrelated donors, the likelihood of fatal graft vs. host disease (GvHD) and/or graft rejection increases from 20% for matched sibling donors to 50% in the cases of matched, unrelated donors and un-matched donors from the patient's family. Further, in cases where an unrelated donor is not matched at one of the six major transplantation antigens, graft rejection and/or fatal GvHD increases to 60%.

GvHD is a disease with significant morbidity. Patients who develop acute GvHD may develop blisters covering most of their skin surface, massive gastrointestinal bleeding or fulminant liver failure and jaundice. Patients who develop chronic GvHD may develop scleroderma that results in joint contractures and skin ulcers, hair loss and a generalized wasting syndrome. Patients with acute or chronic GvHD are immuno-suppressed and at risk for life-threatening opportunistic infections similar to those that develop among AIDS patients.

The removal of T cells from the bone marrow obtained from matched unrelated or unmatched sibling donors results in a decreased incidence of graft vs. host reactions, but an increased incidence of rejection of the allogeneic bone marrow graft by the patient. Thus, lymphocytes, and especially T cells, present in the allogeneic bone marrow graft are important to ensure engraftment in antigenically and genetically mis-matched recipients. T cells present in the allogeneic graft also have an important role in eliminating residual cancer cells in the recipient, a phenomenon termed "graft vs. leukemia effect." The "ideal" donor T cell in an allogeneic bone marrow or stem cell graft would have the ability to prevent graft rejection and mediate the graft vs. leukemia effect without producing GvHD. The potential to successfully transplant T cell-depleted, or stem cell-enriched bone marrow or stem cells from antigenically mis-matched donors to patients without graft rejection or GvHD would greatly extend the availability of bone marrow transplantation to those patients without an antigenically matched sibling donor.

In a dog model of allogeneic bone marrow transplantation, the addition of viable donor lymphocytes to the bone marrow graft resulted in an increased frequency of stable engraftment, from 9% using antigenically mismatched bone marrow alone, to 88%, using a combination of bone marrow and donor lymphocytes. However, all the animals that received donor lymphocytes died of lethal GvHD (Storb et al (1968) "Marrow grafts by combined marrow and leucocyte infusions in unrelated dogs selected by histocompatibility typing" *Transplantation* 6:587–593).

An alternative to infusions of viable donor lymphocytes has been the use of irradiated donor lymphocytic infusions in the post-transplant period. The addition of donor lymphocytes that had been previously irradiated to a dose of 20 Gy (2,000 rads) to allogeneic bone marrow cells did not prevent fatal graft failure when the mixture was administered to lethally irradiated dogs antigenically mismatched for dog leukocyte antigens (DLA), (Deeg et al (1979) "Abrogation of resistance to and enhancement of DLA-nonidentical unrelated marrow grafts in lethally irradiated dogs by thoracic duct lymphocytes", *Blood* 53:552–587).

In genetically unrelated rabbits, a series of five infusions of donor lymphocytes, irradiated to 15 Gy (1,500 rads) one to ten days following the infusion of allogeneic bone marrow cells and irradiated autologous bone marrow cells decreased the rate of graft rejection from 60% to 20%, but only 30% of the treated animals survived more than 100 days with donor derived hematopoietic cells and 40% of animals that received T cell depleted bone marrow followed by irradiated allogenic lymphocytes developed GvHD. (Gratwohl et al. (1987) "Engraftment of T-cell depleted rabbit bone marrow" *Acta haematol.* 77:208–214).

The addition of antigenically matched viable donor lymphocytes obtained from the bone marrow donor and given 1–5 days post-transplant to 43 patients undergoing allogeneic bone marrow transplantation for aplastic anemia resulted in a 14% incidence of graft failure compared to 22% in a similar group of 20 patients who received the bone marrow transplant without additional donor lymphocytes. However, the incidence of acute GvHD was 36% in the group treated with donor lymphocytes compared to a 20% incidence of acute GvHD in the group that received bone marrow cells alone. In both groups, 20% of patients ultimately died of GvHD, (Storb et al (1982) "Marrow transplantation with or without donor buffy coat cells for 65 transfused aplastic anemia patients", *Blood* 59:236–246).

In a clinical report describing the use of irradiated human lymphocytes, 20 patients with hematological malignancies were treated with high-dose chemotherapy and total body irradiation followed by the infusion of T cell-depleted antigenically matched, genetically related allogeneic bone marrow cells. One, three, five, seven and fourteen days following bone marrow transplantation, the patients received infusions of donor lymphocytes, irradiated to 15 Gy (1,500 rads). The authors reported no cases of graft failure, but noted an overall incidence of GvHD of 85% and a 15% incidence of fatal GvHD, (Gratwohl et al. (1988) "Irradiated donor buffy coat following T cell-depleted bone marrow transplants", *Bone marrow transplantation* 3:577–582).

These reports suggest that infusions of irradiated donor lymphocytes are not toxic to recipients of bone marrow transplantation, but do not demonstrate clear efficacy in either preventing graft rejection or GvHD. The present invention overcomes the problems in the art by providing a method of transplanting hematopoietic system reconstituting cells from a donor to an antigenically matched or unmatched, genetically unrelated recipient or an antigenically unmatched, genetically related recipient with successful engraftment in the absence of GvHD.

SUMMARY OF THE INVENTION

The present invention provides a method of transplanting hematopoietic system reconstituting cells from a donor into an allogeneic recipient comprising administering to the recipient, prior to the administration of the hematopoietic system reconstituting cells, an amount of mononuclear cells which are treated so as to render them incapable of proliferating and causing a lethal GvHD effect, but which are effective in enhancing subsequent engraftment of the hematopoietic system reconstituting cells in the recipient; and administering to the recipient an effective amount of hematopoietic system reconstituting cells.

In a specific embodiment, the present invention provides a method of transplanting bone marrow cells into an allogeneic recipient comprising administering to the recipient, one to five days prior to administration of the bone marrow cells, between $0.05 \times 10^6$ and $30 \times 10^6$ cells/kg of body weight of T cells that have been exposed to between 500 and 1000 rads of irradiation; and administering to the recipient between $1.0 \times 10^8$ and $4.0 \times 10^8$ T cell-depleted bone marrow cells/kg of body weight.

DETAILED DESCRIPTION OF THE EMBODIMENTS

The present invention may be understood more readily by reference to the following detailed description of specific embodiments and the Examples included herein.

In one embodiment, the present invention provides a method of transplanting hematopoietic system reconstituting cells from a donor source into an allogeneic recipient comprising administering to the recipient, prior to the administration of the hematopoietic system reconstituting cells, an amount of mononuclear cells which are treated so as to render them incapable of proliferating and causing a lethal GvHD effect, but which are effective in enhancing subsequent engraftment of the hematopoietic system reconstituting cells in the recipient; and administering to the recipient an effective amount of hematopoietic system reconstituting cells.

As used herein, "hematopoietic system reconstituting cells" means a population of cells, preferably human, that possess the capability of dividing and producing progeny that include all of the formed cellular elements of the blood. As used herein, "donor source" means the animal, preferably human, that is the natural source from which the hematopoietic system reconstituting cells are originally removed. Also as used herein, a "recipient" is the animal, typically human, into which the hematopoietic system reconstituting cells will be transplanted. The term "allogeneic" as used herein means that the recipient is not the natural source from which the hematopoietic system reconstituting cells have been removed. Major histocompatability complex antigens (also called human leukocyte antigens, HLA) are protein molecules expressed on the surface of cells that confer a unique antigenic identity to these cells. MHC/HLA antigens are target molecules that are recognized by certain immune effector cells [T-cells and natural killer (NK) cells] as being derived from the same source of hematopoietic reconstituting stem cells as the immune effector cells ("self") or as being derived from another source of hematopoietic reconstituting cells ("non-self").

Mononuclear cells are cells of the hematopoietic system identified by a round, nonsegmented nucleus. Mononuclear cells can include T cells, NK cells, monocytes, mixtures of T cells, NK cells or monocytes.

Properties of T cells include the expression of a complex of proteins on their cell surface that include the CD3 antigen and the T cell receptor (TCR) that can bind to MHC/HLA molecules expressed on the surface of other cells. The presence of the CD3/TCR complex allows T cells to recognize cells from genetically different individuals as expressing "non-self" MHC/HLA antigens and to recognize virally infected cells and tumor cells from the same individual as expressing "altered self" MHC/HLA antigens. T cells are able to bind to and kill cells that express "non-self" and "altered self" MHC/HLA by the activation of specific cytolytic enzymes; they regulate (including stimulation and inhibition) T cell and B cell proliferation and antibody production in response to a specific antigen; they release protein molecules called cytokines that stimulate or inhibit the immune response; and they undergo multiple rounds of cell division and produce daughter cells with similar biologic properties as the parent cell. Examples of T cells with some attributes of NK cells include cells that express both the CD3 (T cell specific) and the CD56 (NK cell specific) antigens.

Properties of NK cells include: the expression of antigens on their cell surface that include one or more of the following: CD16, CD56, and CD57 and the absence of the alpha/beta or gamma/delta TCR complex expressed on the cell surface; the ability to bind to and kill cells that fail to express "self" MHC/HLA antigens by the activation of specific cytolytic enzymes; the ability to kill tumor cells from a genetically unrelated individual; the ability to release protein molecules called cytokines that stimulate or inhibit the immune response; and the ability to undergo multiple rounds of cell division and produce daughter cells with similar biologic properties as the parent cell.

Properties of monocytes include the ability to engulf (phagocytosis) bacteria and "non-self" cells; the elaboration of cytokines that stimulate T cells and NK cells; the release of molecules that cause inflammation; and the presentation of antigens to T cells.

The mononuclear cells are "treated so as to render them incapable of proliferating and causing a lethal GvHD effect." As used herein, this phrase means that the mononuclear cells can be treated, for example by exposure to a source of ionizing radiation, which will have the effect of preventing lethal GvHD. It is believed that the treatment sufficiently hinders the mononuclear cell proliferation such that they do not cause a lethal GvHD in the patient. Sources of ionizing radiation can include but are not limited to gamma radiation produced by the nuclear decay of a radio-isotope (Till and McCulloch, 1961, "A direct measurement of the radiation sensitivity of normal mouse bone marrow cells", *Radiation Research*, 14:213–222) and a linear accelerator which produces high energy X-rays (Gratwohl et al. (1988), "Irradiated buffy coat following T cell depleted bone marrow transplants", *Bone Marrow Transplantation*, 3:577–582). Using gamma radiation as the source of the ionizing radiation, the mononuclear cells, in one example, can be irradiated with between 250 and 2000 rads of radiation. An alternative range of irradiation doses is between 500 and 1500 rads of irradiation, with 500 to 1000 rads of irradiation being another range. In another example, the mononuclear cells can also be irradiated with gamma radiation using any range of any values between 250 and 5000 rads, for example, 350 and 1900, 450 and 1800, 550 and 1700, etc. or combinations thereof (e.g., 250 and 1900).

Alternatively, the mononuclear cells can be treated with cytotoxic chemotherapeutic drugs to render the cells incapable of proliferating and causing a lethal GvHD. Cytotoxic chemotherapeutic drugs act by cross-linking DNA or otherwise interfering with normal cellular metabolism so as to render cells incapable of proliferating (Chabner (1993) "Anticancer Drugs" in *Cancer: Principles and Practice of Oncology, Fourth Edition*, eds. DeVita, Hellman, and Rosenberg. pp. 325–417. J. B. Lippincott publishers, Philadelphia). Examples of such cytotoxic chemotherapeutic drugs that could be employed in the present invention include, but are not limited to, mitomycin C, bleomycin, actinomycin D, fludarabine, doxirubicin, daunorubicin, mitoxanthrone, cytarabine, streptozocin and amsacrine. The mononuclear cells are incubated with a sufficient concentration of the cytotoxic drug so as to result in their eventual death. For example, $5 \times 10^7$ mononuclear cells/ml can be incubated with 50 ug/ml mitomycin C in phosphate buffered saline for 20 minutes at 37°. Mitomycin C enters the mononuclear cells and acts to cross-link DNA. Unbound mitomycin C is then removed by diluting the cell suspension with PBS, centrifuging the mixture at 300×g for 5 minutes and removing the supernatant. Fresh PBS is added to the cell pellet and the washing procedure is repeated two additional times. The cell pellet is then resuspended in PBS or a similar physiologic salt solution.

The mononuclear cells are treated, for example, by either ionizing radiation or cytotoxic chemotherapeutic drugs to render the cells substantially incapable of proliferating but such that the mononuclear cells are effective in enhancing subsequent engraftment of the hematopoietic system reconstituting cells in the recipient, for example, by neutralizing restricting host cells. This enhancement may be due to mononuclear cells conditioning the recipient to successfully accept the transplanted cells without proliferating in the recipient and mounting an immune response against the recipient's cells. The mononuclear cells can also exert a graft versus leukemia effect by which they aid in the elimination of residual cancer cells in the recipient.

The treated mononuclear cells can be administered to the recipient at any time prior to the administration of the hematopoietic system reconstituting cells and preferably are administered up to ten days prior to administration of the hematopoietic system reconstituting cells. Most preferably, the treated mononuclear cells are administered to the recipient between one and five days prior to the administration of the hematopoietic system reconstituting cells. Any range of treatment, e.g., one to nine, two to eight, three to seven, one to two, one to three, zero to one, zero to two days, etc. are also provided.

The hematopoietic system reconstituting cells and the treated mononuclear cells can be from the same donor source or they can be from different donors. These donor source cells include cells which are propagated in vitro or derived in vitro from a less differentiated cell type of the donor source, for example, from a yolk sac or other embryonic fetal tissue source such as embryonic stem cells.

The amount of treated mononuclear cells administered to the recipient, in one example, can be between $0.05 \times 10^6$ and $30 \times 10^6$ cells/kg of the recipient's body weight. Subranges of treated mononuclear cells are also provided, for example 5.0 to $25 \times 10^6$, 10 to $20 \times 10^6$, 5.0 to $20 \times 10^6$, etc.

The hematopoietic system reconstituting cells administered to the recipient can, in one example, be present in a source population of between $0.2 \times 10^8$ and $4.0 \times 10^8$, or ranges there between, donor bone marrow cells/kg of the recipient's body weight. The bone marrow cells can be obtained from the donor by standard bone marrow aspiration techniques known in the art. Bone marrow cells are removed from the donor by placing a hollow needle into the marrow space and withdrawing a quantity of marrow cells by aspiration.

Alternatively, the hematopoietic system reconstituting cells administered to the recipient can, in one example, be present in a source population of between $1.0 \times 10^8$ and $40 \times 10^8$, or ranges there between, donor cytokine mobilized peripheral blood stem cells/kg of recipient's body weight. Peripheral blood cells can be obtained from the donor, for example, by standard phlebotomy or apheresis techniques. Phlebotomy is performed by placing a hollow needle into a vein and withdrawing a quantity of whole blood using aspiration or gravity. Apheresis is performed in a similar manner to phlebotomy except the whole blood is anticoagulated and then separated into the constituent formed cellular elements by centrifugation. The mononuclear cell fraction is retained and the remaining plasma and other cellular elements (red blood cells, granulocytes, platelets) are returned to the donor by intravenous infusion.

Peripheral blood stem cells can be cytokine mobilized by injecting the donor with hematopoietic growth factors such as Granulocyte colony stimulating factor (G-CSF), granulocyte-monocyte colony stimulating factor (GM-CSF), stem cell factor (SCF) subcutaneously or intravenously in amounts sufficient to cause movement of hematopoietic stem cells from the bone marrow space into the peripheral circulation. The hematopoietic reconstituting cells can also be derived from fetal or embryonic human tissue that is processed and/or cultured in vitro so as to increase the numbers or purity of primitive hematopoietic elements.

The hematopoietic system reconstituting cells administered to the recipient can be T cell-depleted to prevent the development of GvHD. The cell population is depleted of T cells by one of many methods known to one skilled in the art (Blazer et al, (1985) "Comparison of three techniques for the ex vivo elimination of T cells from human bone marrow." *Experimental Hematology* 13:123–128) or by using affinity chromatography, as described below. In addition, the hematopoietic system reconstituting cells administered to the recipient can also be hematopoietic system cells that have been enriched from the source population. The source population can be either donor bone marrow cells or donor peripheral blood cells. The hematopoietic system reconstituting cells can be enriched from the source population by selecting cells that express the CD34 antigen, using combinations of density centrifugation, immuno-magnetic bead purification, affinity chromatography, and fluorescent activated cell sorting, known to those skilled in the art (Baum, C. M., I. L. Weissman et al., (1992) "Isolation of a candidate human hematopoietic stem-cell population" *Proc. Natl. Acad. Sci. U.S.A.* 89:2804–8; Lansdorp, P. M., H. J. Sutherland et al., (1990) "Selective expression of CD45 isoforms on functional subpopulations of CD34+ hematopoietic cells from human bone marrow." *J Exp. Med.* 172:363–6; Sato, N., K. Sawada et al, (1991) "Purification of human marrow progenitor cells and demonstration of the direct action of macrophage colony-stimulating factor on colony-forming unit-macrophage" *Blood* 78:967–74; Smith, C., C. Gasparetto et al., (1991) "Purification and partial characterization of a human hematopoietic precursor population" *Blood* 77:2122–8; Udomsakdi, C., C. J. Eaves et al., (1991) "Separation of functionally distinct subpopulations of primitive human hemtapoietic cells using rhodamine-123" *Exp. Hematol.* 19:338–42; Udomsakdi, C., P. M. Lansdorp et al., (1992) "Characterization of primitive hematopoietic cells in normal human peripheral blood" *Blood* 80:2513–21.

The treated mononuclear cells and hematopoietic system reconstituting cells are typically administered to the recipient in a pharmaceutically acceptable carrier by intravenous infusion. Carriers for these cells can include but are not limited to solutions of phosphate buffered saline (PBS) containing a mixture of salts in physiologic concentrations.

The recipient can be treated with antibodies or antisera intended to deplete residual T cells or NK cells. Examples include the administration of 100 µl of antiasialo antisera to mice by intravenous or intraperitoneal injection one to three days prior to the administration of allogeneic bone marrow cells, a treatment that enhances the engraftment of the mice by antigenically mismatched and genetically unrelated tumor cells (Waller et al (1991) "Growth of primary T-cell non-Hodgkin's lymphomata in SCID-hu mice: requirement for a human lymphoid microenvironment", *Blood* 78(10): 2650–65). Another example includes the intravenous administration of anti-thymocyte globulin to human patients one to five days prior to the intraveneous infusion of allogeneic bone marrow cells (Storb et al. (1994) "Cyclophosphamide combined with antithymocyte globulin in preparation for allogeneic marrow transplants in patients with aplastic anemia", *Blood* 84(3):941–9).

In a more specific embodiment, the present invention provides a method of transplanting bone marrow cells from a donor into an allogeneic recipient comprising administering to the recipient, one to five days prior to administration of the bone marrow cells, between $0.05 \times 10^6$ and $30 \times 10^6$ cells/kg of the recipient's body weight of T cells that have been exposed to between 500 and 1000 rads of gamma irradiation; and administering to the recipient between $1.0 \times 10^8$ and $4.0 \times 10^8$ cells/kg of the recipient's body weight of T cell-depleted bone marrow cells.

The present invention also provides a method of treating a cancer using mononuclear cells from a donor source into a non-autologous recipient. The method utilizes the protocol of administering mononuclear cells as described above. However, the mononuclear cells can be used to treat the cancer even in the absence of a hematopoietic cell transplantation. Thus, the step of administering hematopoietic system reconstituting cells is not necessary to treat a cancer.

Preferably, for treating a cancer an allogeneic transfer of mononuclear cells is utilized although the transfer can also be xenogeneic. In either context the tumor antigen or whole cells containing the antigen can be utilized to prime the donor or cells from the donor prior to transfer to the recipient. Current Protocol in Immunology ed. J. E. Coligan et al., John Wiley and Sons (1994).

Any cancer can be treated using this method. These cancers include skin, brain, squamous cell carcinoma, sarcoma, esophageal, stomach, liver, kidney, colon, bladder, prostate, ovarian, uterine, testicular, neuroendocrine, bone, and pancreatic cancer. The method is especially useful for hematopoietic cell cancers such as leukemias, lymphomas and multiple myeloma.

EXAMPLES

Animals. B 10 R.III (H2Kr) mice, aged eight to ten weeks, were purchased from Charles River/Jackson Laboratories. C57B1/6 (H2Kb Thy 1.2) and BA (H2Kb Thy 1.1) mice were bred and maintained in sterile housing at the Emory University Animal Care Facility. Drinking water was acidified to a pH of 2.5.

Donor Cell Preparations. All manipulations of cells were performed with sterile Hanks Buffered Saline Solution (HBSS) containing 3% heat-inactivated fetal bovine mice by removing the femora and tibia. The bone marrow space was flushed with medium using a 25 gauge needle, followed by repeated pipetting to yield a single-cell suspension. Spleenocytes were harvested from BA (H2Kb Thy 1.1) mice by removing the spleen and placing it in a small petri dish. A single cell suspension was generated by flushing the spleen with medium using a 25 gauge needle followed by repeated pipetting.

T Cell Manipulations. Bone marrow cells at a concentration of $2 \times 10^7$ cells per milliliter were incubated with biotinylated αCD3 antibody (Pharmingen, San Diego, Calif.) at a saturating concentration of antibody on ice for 20 minutes, then washed with ten volumes of HBSS/FBS and collected by centrifugation. The cell pellets were suspended in 100 µl of Streptavidin Microbeads (Miltenyi Biotech GmbH) and 200 µl degassed HBSS. This solution was incubated on ice for 20 minutes, then washed as previously described. The cells were run over a Mini Macs magnetic separation column (Miltenyi Biotech, Gmbh). The first fraction collected was depleted of CD3+ cells (T cell depleted fraction). The column was removed from the magnetic source and CD3+ cells were eluted by washing the column with 0.5 ml HBSS/FBS.

Irradiation of spleen cells. Spleen cell suspensions were irradiated to 1000 rads in a single fraction at a dose rate of 1.462 rads/sec (0.01462 Gy/sec).

Antiasialo treatment. Recipient mice were injected intravenously with 100 µl (0.1 ml) of antiasialo antisera.

Irradiation mad reconstitution. Recipient animals B10RJII (H2Kr) were exposed to 10 Gy (1000 rads) of radiation from a $Cs^{137}$ source (Gamacell Irradiator, Canada) at a dose rate of 0.01462 cGy/sec (1.462 rads/sec), with the total dose being delivered in two equal fractions separated by a five hour rest. Bone marrow and spleen cell suspensions were transplanted to irradiated animals by retroorbital injection under methoxyflurane anesthesia. The recipient animals were maintained on oral aqueous antibiotics (Neomycin Sulfate Polymyxin B Sulfate 6000 units/mg, Sigma Chemical, St. Louis) for four weeks after the delivery of the radiation.

Analysis of transplant recipients. Beginning at one month after transplant, mice were anesthetized with methoxyflurane and about 200 µl of peripheral blood was collected from the retroorbital sinus into 400 µl of HBSS plus 100 U/ml sodium heparin. A 2 ml volume of 3% Dextran T500 (Pharmacia LKB, Piscataway, N.J.) in HBSS was added to each blood sample and the mixture was incubated for 20 min at room temperature to allow sedimentation of red blood cells (RBC). The upper layer of RBC-depleted fluid was transferred to a new tube. Cells were collected from this layer by centrifugation and resuspended in 2 ml of cold 0.2% NaCl for one minute followed by the addition of 2 ml of cold 1.6% NaCl to restore isotonicity. Cells were collected by centrifugation, then resuspended in HBSS/FBS at a cell concentration of approximately $1 \times 10^6$ cells/100 µl for immunofluorescent staining. Donor and host-derived cells were distinguished with monoclonal antibodies specific for the MHC (H2Kb). Dual-color immunofluorescence, using a fluorescein-conjugated anti-Thy 1.1 reagent and allophycocyanin-conjugated anti-Thy 1.2 reagent was performed to enumerate donor-derived T cells from bone marrow (Thy 1.2) and spleen (Thy 1.1).

Results. Table 1 shows the fraction of mice surviving thirty days after receiving a lethal dose of ionizing radiation followed by intravenous infusion of a small number (500,000 cells; $0.2 \times 10^8$ cells/kg) of mouse marrow cells. The survival was greatest (80%) among mice that received bone marrow cells from genetically identical (syngeneic) litter mates, and lowest (0%) among mice that received bone marrow from genetically dissimilar (allogeneic) donors. The allogeneic donors expressed the "b" antigen on their MHC molecules while the recipients expressed the "r" antigen.

The two strains of mice are completely (fully) mismatched at the MHC antigen loci. An analogous situation in humans would be donors and patients mismatched at all six of the HLA antigen loci. It is worth noting that mortality is 60% due to graft failure and/or GvHD for genetically related human donors and patients mismatched at twoout of six HLA antigens.

The survival of mice that received allogeneic bone marrow cells was increased to 80% by the co-administration of unirradiated allogeneic spleen cells; however these recipient mice were at risk for developing GvHD as assessed by the survival of large numbers (+++) of mature T cells in their peripheral blood derived from the infused spleenocytes. Mice that received allogeneic bone marrow cells in combination with irradiated spleen cells had a survival that was intermediate between the group that received syngeneic bone marrow and the group that received allogeneic bone marrow cells alone. Recipients of irradiated spleen cells did not have any detectable spleen-derived T cells in their peripheral blood, and are at much lower risk for GvHD. The addition of a single dose of irradiated spleen cells co-administered with the allogeneic bone marrow cells increased survival of recipient mice to 20%; the administration of two doses of irradiated spleen cells, (the first one day prior to the administration of allogeneic bone marrow cells and an additional dose co-administered with the allogeneic bone marrow cells) increased survival to 41%. The injection of anti-asialo antisera preceding the administration of two doses of irradiated spleen cells and the allogeneic bone marrow increased survival to 60%. The function of anti-asialo antisera is to cause in vivo depletion of host NK cells, further reducing the resistance of the irradiated recipient to engraftment by fully allogeneic hematopoietic reconstituting cells.

Administration of treated mononuclear cells and hematopoietic system reconstituting cells to a human subject. A patient, diagnosed with a disorder for which transplantation of hematopoietic system reconstituting cells is indicated, can be given about $5 \times 10^6$ treated mononuclear cells/kg isolated from the peripheral blood of the donor by apheresis about two days prior to the administration of the hematopoietic system reconstituting cells. After administration of the treated mononuclear cells, the patient can be given hematopoietic system reconstituting cells either in a source population of about $5 \times 10^6$ CD34+ cells/kg isolated by apheresis from the donor's peripheral blood following treatment with GCSF or an equivalent cytokine, or about $2 \times 10^6$ CD34+ cells/kg present in donor bone marrow obtained by harvesting bone marrow cells. The hematopoietic system reconstituting cells administered to the patient can be T cell-depleted or CD34+ cell-enriched from the source population. $10^6$ CD34+ cells/kg present in donor bone marrow obtained by harvesting bone marrow cells. The hematopoietic system reconstituting cells administered to the patient can be T cell-depleted or CD34+ cell-enriched from the source population.

Irradiated allogeneic donor lymphocytes have an antileukemic effect in mice without producing graft vs. host disease. We have tested the anti-leukemic activity of irradiated allogeneic lymphocytes administered prior to and following allogeneic bone marrow transplantation (BMT) in mice. Methods: Lethally irradiated C57BL6 mice (H2K, Ly 5.2) were transplanted with $0.5 \times 10^6$ T-cell depleted (TCD) BM cells from MHC mismatched B10.BR ($H2K^K$) donors along with a lethal dose of C1498 myeloid leukemia cells from a congenic strain of Ly 5.1+C57BL6 mice. Allogeneic spleen cells ($H2K^K$) were administered 24 hours prior to BMT and then concomitantly with the TCD BM graft. Results: Mice receiving C1498 leukemia cells and TCD BM alone had a median survival time of 9 days with none of the mice surviving past day 22. The addition of two doses of $15 \times 10^6$ non-irradiated allogeneic spleen cells to mice receiving C1498 leukemia cells and TCD BM decreased the median survival time to 6 days, with mice succumbing to GvHD. The administration of two doses of $15 \times 10^6$ irradiated (7.5 Gy) allogeneic spleen cells significantly increased the median survival time to 22 days ($p<0.01$), with 40% of recipients surviving past day 30 without evidence of leukemia. Among the mice that died in the group receiving irradiated spleen cells, 66% died of bone marrow hypoplasia and graft failure without evidence of leukemia in their blood, spleen, or bone marrow. Irradiated allogeneic lymphocytes retain an anti-leukemic activity in vivo without resulting in significant GvHD.

Throughout this application, various publications are referenced. The disclosures of these publications in their entireties are hereby incorporated by reference into this application in order to more fully describe the state of the art to which this invention pertains.

TABLE 1

30 day survivial for mice that received a lethal dose of radiation followed by transplantation with $0.5 \times 10^6$ bone marrow cells

| | | | | | | |
|---|---|---|---|---|---|---|
| Day −2 | | | | | | anti asialo anti-sera |
| Day 0 | Syngeneic Bone marrow | Allogeneic Bone marrow | Allogeneic Bone marrow + $5 \times 10^6$ allo spleen | Allogeneic Bone marrow + $5 \times 10^6$ irradiated allo spleen | $5 \times 10^6$ irradiated allo spleen | $5 \times 10^6$ irradiated allo spleen |
| Day 1 | | | | | Allogeneic Bone marrow + $5 \times 10^6$ irradiated | Allogeneic Bone marrow + $5 \times 10^6$ irradiated |

TABLE 1-continued 30 day survivial for mice that received a lethal dose of radiation followed by transplantation with 0.5 × 10⁶ bone marrow cells

|  |  |  |  |  | allo spleen | allo spleen |
|---|---|---|---|---|---|---|
| Day 30 Survival (%) | 80% | 0% | 80% | 20% | 41% | 60% |
| Nubmer per group | n = 15 | n = 24 | n = 10 | n = 5 | n = 17 | n = 20 |
| Donor-derived Hematopoietic Reconstruction | N/A | N/A | 100% | 100% | 100% | 100% |
| Presence of T-cells from allo spleen | N/A | N/A | +++ | – | – | – |

What is claimed is:

1. A method of treating a cancer in a non-autologous recipient with mononuclear cells from a donor source, comprising administering to the recipient an amount of mononuclear cells from a donor source which are treated so as to render them incapable of proliferating and causing a lethal graft versus host disease effect, but which are effective in treating the cancer in the recipient.

2. The method of claim 1, wherein the mononuclear cells are T cells.

3. The method of claim 1, wherein the mononuclear cells are natural killer cells.

4. The method of claim 1, wherein the mononuclear cells are a mixture of T cells and natural killer cells.

5. The method of claim 1, wherein recipient is allogeneic.

6. The method of claim 1, wherein the mononuclear cells are treated by exposure to a source of ionizing radiation.

7. The method of claim 6, wherein the source of ionizing radiation is gamma radiation produced by the nuclear decay of a radio-isotope.

8. The method of claim 6, wherein the source of ionizing radiation is a linear accelerator which produces high energy X-rays.

9. The method of claim 6, wherein the amount of irradiation is between 250 and 2000 rads.

10. The method of claim 6, wherein the amount of irradiation is between 500 and 1500 rads.

11. The method of claim 6, wherein the amount of irradiation is between 500 and 1000 rads.

12. The method of claim 1, wherein the amount of treated mononuclear cells administered to the recipient is between $0.05 \times 10^6$ and $30 \times 10^6$ cells/kg of the recipient's body weight.

13. The method of claim 1, wherein the cancer is a hematopoietic cell cancer.

14. The method of claim 13, wherein the hematopoietic cell cancer is leukemia.

15. The method of claim 1, wherein the mononuclear cells are produced by exposure to a source of ionizing radiation.

16. The method of claim 15, wherein the source of ionizing radiation is gamma radiation produced by the nuclear decay of a radio-isotope.

17. The method of claim 15, wherein the source of ionizing radiation is a linear accelerator which produces high energy X-rays.

18. The method of claim 15, wherein the amount of irradiation is between 250 and 2000 rads.

19. The method of claim 15, wherein the amount of irradiation is between 500 and 1500 rads.

20. The method of claim 15, wherein the amount of irradiation is between 500 and 100 rads.

21. The method of claim 15, wherein the mononuclear cells are T cells.

22. The method of claim 15, wherein the mononuclear cells are natural killer cells.

23. The method of claim 15, wherein the mononuclear cells are a mixture of T cells and natural killer cells.

24. A method of transplanting hematopoietic system reconstituting cells from a donor source into an allogeneic recipient and producing an anti-cancer effect in the recipient, comprising:
   a) administering to the recipient, prior to or on the same day of the administration of the hematopoietic system reconstituting cells, an amount of mononuclear cells from a donor source which are treated so as to render them incapable of proliferating and causing a lethal graft versus host disease effect, but which are effective in enhancing subsequent engraftment of the hematopoietic system reconstituting cells and producing an anti-cancer effect in the recipient; and
   b) administering to the recipient an effective amount of hematopoietic system reconstituting cells.

25. The method of claim 24, wherein the mononuclear cells are T cells.

26. The method of claim 24, wherein the mononuclear cells are natural killer cells.

27. The method of claim 24, wherein the mononuclear cells are a mixture of T cells and natural killer cells.

28. The method of claim 24, further comprising depleting the recipient's T cells and natural killer cells prior to administration of the hematopoietic system reconstituting cells.

29. The method of claim 24, wherein the mononuclear cells are treated by exposure to a source of ionizing radiation.

30. The method of claim 29, wherein the source of ionizing radiation is gamma radiation produced by the nuclear decay of a radio-isotope.

31. The method of claim 29, wherein the source of ionizing radiation is a linear accelerator which produces high energy X-rays.

32. The method of claim 29, wherein the amount of irradiation is between 250 and 2000 rads.

33. The method of claim 29, wherein the amount of irradiation is between 500 and 1500 rads.

34. The method of claim 29, wherein the amount of irradiation is between 500 and 1000 rads.

35. The method of claim 24, wherein the treated mononuclear cells are administered to the recipient up to ten days prior to administration of the hematopoietic system reconstituting cells.

36. The method of claim 24, wherein the treated mononuclear cells are administered to the recipient between one and five days prior to the administration of the hematopoietic system reconstituting cells.

37. The method of claim 24, wherein the hematopoietic system reconstituting cells and the treated mononuclear cells are from the same donor source.

38. The method of claim 24, wherein the amount of treated mononuclear cells administered to the recipient is between $0.05 \times 10^6$ and $30 \times 10^6$ cells/kg of the recipient's body weight.

39. The method of claim 24, wherein the hematopoietic system reconstituting cells administered to the recipient are present in a source population of between $0.2 \times 10^8$ and $4.0 \times 10^8$ donor bone marrow cells/kg of recipient's body weight.

40. The method of claim 24, wherein the hematopoietic system reconstituting cells administered to the recipient are present in a source population of between $1.0 \times 10^8$ and $40 \times 10^8$ donor cytokine mobilized peripheral blood stem cells/kg of recipient's body weight.

41. The method of claim 24, wherein the hematopoietic system reconstituting cells that are administered to the recipient are T cell-depleted.

42. The method of claim 24, wherein the hematopoietic system reconstituting cells that are administered to the recipient are hematopoietic stem cell enriched from the source population.

43. The method of claim 24, wherein the cancer is a hematopoietic cell cancer.

44. The method of claim 43, wherein the hematopoietic cell cancer is leukemia.

* * * * *